(12) United States Patent
Habib et al.

(10) Patent No.: US 7,713,849 B2
(45) Date of Patent: May 11, 2010

(54) METALLIC NANOWIRE ARRAYS AND METHODS FOR MAKING AND USING SAME

(75) Inventors: Youssef M. Habib, Lancaster, PA (US); John Steinbeck, Fitzwilliam, NH (US)

(73) Assignee: Illuminex Corporation, Lancaster, PA (US)

( * ) Notice: Subject to any disclaimer, the term of this patent is extended or adjusted under 35 U.S.C. 154(b) by 479 days.

(21) Appl. No.: 11/206,632

(22) Filed: Aug. 18, 2005

(65) Prior Publication Data

US 2006/0038990 A1  Feb. 23, 2006

Related U.S. Application Data

(60) Provisional application No. 60/603,203, filed on Aug. 20, 2004.

(51) Int. Cl.
  *H01L 21/00* (2006.01)
(52) U.S. Cl. .......................... 438/479; 977/762; 438/48
(58) Field of Classification Search ......... 438/478–483, 438/48; 977/762; 216/2
  See application file for complete search history.

(56) References Cited

U.S. PATENT DOCUMENTS

| | | | |
|---|---|---|---|
| 4,777,019 A | 10/1988 | Dandekar | |
| 5,192,507 A | 3/1993 | Taylor et al. | |
| 5,266,498 A | 11/1993 | Tarcha et al. | |
| 5,445,972 A | 8/1995 | Tarcha et al. | |
| 5,609,907 A | 3/1997 | Natan | |
| 5,811,917 A * | 9/1998 | Sekinger et al. | 313/336 |
| 6,149,868 A | 11/2000 | Natan et al. | |
| 6,219,137 B1 | 4/2001 | Vo-Dinh | |
| 6,278,231 B1 * | 8/2001 | Iwasaki et al. | 313/310 |
| 6,325,904 B1 | 12/2001 | Peeters | |
| 6,699,724 B1 | 3/2004 | West et al. | |
| 6,750,016 B2 | 6/2004 | Mirkin et al. | |
| 6,828,786 B2 | 12/2004 | Scherer et al. | |
| 6,861,263 B2 | 3/2005 | Natan | |
| 6,884,587 B2 | 4/2005 | Ford et al. | |
| 6,890,764 B2 | 5/2005 | Chee et al. | |
| 7,267,859 B1 * | 9/2007 | Rabin et al. | 428/131 |
| 7,288,419 B2 * | 10/2007 | Naya | 438/20 |
| 2003/0231304 A1 * | 12/2003 | Chan et al. | 356/301 |
| 2004/0023046 A1 * | 2/2004 | Schlottig et al. | 428/469 |
| 2004/0063214 A1 * | 4/2004 | Berlin et al. | 436/94 |
| 2004/0144985 A1 * | 7/2004 | Zhang et al. | 257/79 |
| 2004/0213307 A1 * | 10/2004 | Lieber et al. | 372/39 |
| 2005/0077184 A1 * | 4/2005 | Lazarenko-Manevich et al. | 205/105 |

(Continued)

OTHER PUBLICATIONS

Xu, H. et al., "Electromagnetic Contributions to Single-Molecule Sensitivity in Surface-Enhanced Raman Scattering," Physical Review, 62, 4318-4323, (2000).

(Continued)

*Primary Examiner*—Savitri Mulpuri
(74) *Attorney, Agent, or Firm*—Ted Sabety; Sabety + associates, PLLC

(57) ABSTRACT

Freestanding metallic nanowires attached to a metallic substrate are disclosed. A method of creating the nanowire structure using an anodized layer is presented. In one embodiment an optical SERS sensor is formed. The sensor head has at least one array of nanowires chemically functionalized to recognize molecules of interest. A method of forming a SERS sensor and using the sensor to analyze a sample is presented.

22 Claims, 16 Drawing Sheets

U.S. PATENT DOCUMENTS

2005/0136608 A1* 6/2005 Mosley ........................ 438/381
2006/0054881 A1* 3/2006 Li et al. ........................ 257/19
2006/0289351 A1* 12/2006 Xiao et al. ............. 210/500.25

OTHER PUBLICATIONS

Shipway, A., Katz, E., and Willner, I., "Nanoparticle Arrays on Surfaces for Electronic, Optical, and Sensor Applications," ChemPhysChem, 1, 18-52, (2000).

Efrima, S. and Bronk, B.V., "Silver Colloids Impregnating or Coating Bacteria," J. Physical Chem. B, 102, 5947-5950, (1998).

Li, X. et al., "Mercaptoacetic Acid-Capped Silver Nanoparticles Colloid: Formations, Morphology, and SERS Activity," Langmuir, 19, 4285-4290, (2003).

Kneipp, K. et al., "Near-Infrared Surface-Enhanced Raman Scattering (NIR SERS) on Colloidal Silver and Gold," Applied Spectroscopy, 48, 951-955, (1994).

Grubisha, D. et al., "Femtomolar Detection of Prostate-Specific Antigen: An Immunoassay Based on Surface-Enhanced Raman Scattering and Immunogold Labels," Analytical Chemistry, 75, 5936-5943, (2003).

Felidji, N. et al., "Controlling the Optical Response of Regular Arrays of Gold Particles for Surface-Enhanced Raman Scattering," Physical Review B, 65, 075419, (2002).

Felidji, N. et al., "Gold Particle Interaction in Regular Arrays Probed by Surface Enhanced Raman Scattering," J. Chem. Phys., 120, 7141-7146, (2004).

Tao, A. et al., "Langmuir-Blodgett Silver Nanowire Monolayers for Molecular Sensing Using Surface-Enhanced Raman Spectroscopy," Nano Letters, 3, 1229-1233, (2003).

Saito, Y. et al., "A Simple Method for the Preparation of Silver Surfaces for Efficient SERS," Langmuir, 18, 2959-2961, (2002).

Vo-Dinh, T. et al., "Surface-Enhanced Raman Scattering (SERS) Method and Instrumentation for Genomics and Biomedical Analysis," Journal of Raman Spectroscopy, 30, 785-793, (1999).

Aroca, R. et al., "Silver Nanowire Layer-by-Layer Films as Substrates for Surface-Enhanced Raman Scattering," Anal. Chem., 77, 378-382, (2005).

Jeong, D., Zhang, Y., and Moskvits, M., "Polarized Surface Enhanced Raman Scattering from Aligned Silver Nanowire Rafts," J. Phys. Chem. B, 108, 12724-12728, (2004).

Yao, J.L. et al., "A Complementary Study of Surface-Enhanced Raman Scattering and Metal Nanorod Arrays," Pure Appl. Chem., 72, 221-228, (2000).

Soumahoro, T., "Surface-Enhanced Raman Scattering Substrates: Highly Sensitive Sensors for the Detection of Adsorbate Molecules," NNIN REU Research Accomplishments, 128-129, (2004).

Vo-Dinh, T., "Biosensors, Nanosensors, and Biochips: Frontiers in Environmental and Medical Diagnostics," The 1st International Symposium on Micro and Nano Technology, 1-6, (2004).

Cao, Y.C. et al., "Raman Dye-Labeled Nanoparticle Probes for Proteins," J. Am. Chem. Soc., 125, 14676-14677, (2003).

Haynes, C. and Van Duyne, R., "Plasmon-Sampled Surface-Enhanced Raman Excitation Spectroscopy," J. Phys. Chem. B, 107, 7426-7433, (2003).

Shafer-Peltier, K. et al., "Toward a Glucose Biosensor Based on Surface-Enhanced Raman Scattering," J. AM. Chem. Soc., 125, 588-593, (2003).

Huang, J., Li, C., and Liang, Y., "FT-SERS Studies on Molecular Recognition Capabilities of Monolayers of Novel Nucleolipid Amphiphiles," Langmuir, 16, 3937-3940, (2000).

Kneipp, K. et al., "Single Molecule Detection Using Surface-Enhanced Raman Scattering (SERS)," Physical Review Letters, 78, 1667-1670, (1997).

Bjerneld, E. et al., "Single-Molecule Surface-Enhanced Raman and Fluorescence Correlation Spectroscopy of Horseradish Peroxidase," J. Phys. Chem. B, 106, 1213-1218, (2002).

Jiang, J. et al., "Single Molecule Raman Spectroscopy at the Junctions of Large Ag Nanocrystals," J. Phys. Chem. B, 107, 9964-9972, (2003).

Kneipp, K. et al., "Surface-Enhanced Raman Scattering (SERS)—A New Tool for Single Molecule Detection and Identification," Bioimaging, 6, 104-110, (1998).

Kneipp, K. et al., "Ultrasensitive Chemical Analysis by Raman Spectroscopy," Chem. Rev., 99, 2957-2975, (1999).

Yonzon, C.R. et al., "A Glucose Biosensor Based on Surface-Enhanced Raman Scattering: Improved Partition Layer, Temporal Stability, Reversibility, and Resistance to Serum Protein Interference," Anal. Chem., 76, 78-85, (2004).

Nie, S. and Emory, S., "Probing Single Molecules and Single Nanoparticles by Surface-Enhanced Raman Scattering," Science, 275, 1102-1106, (1997).

Tian, Z., Ren, B., and Wu, D., "Surface-Enhanced Raman Scattering: From Noble to Transition Metals and from Rough Surfaces to Ordered Nanostructures," 106, 9463-9483, (2002).

Haes, A. and VanDuyne, R., "A Nanoscale Optical Biosensor: Sensitivity and Selectivity of an Approach Based on the Localized Surface Plasmon Resonance Spectroscopy of Triangular Silver Nanoparticles," J. Am. Chem. Soc., 124, 10596-10604, (2002).

Van Duyne, R.P. et al., "Nanoparticle Optics: Sensing with Nanoparticle Arrays and Single Nanoparticles," Proceedings of SPIE, 5223, 197-207 (2003).

Sasaki, K.Y. and Talbot, J.B., "Electrodeposition of Iron-Group Metals and Binary Alloys from Sulfate Baths," J.Electrochem.Soc., 145, 981-990 (1998).

Zech, N. Podlaha, E.J., and Landolt, D., "Anomolous Codeposition of Iron Group Metals," 146, 2886-2891 (1999).

* cited by examiner

METALLIC NANOWIRE ARRAYS AND METHODS FOR MAKING AND USING SAME

This nonprovisional patent application claims priority from provisional patent application Ser. No. 60/603,203, filed Aug. 20, 2004, entitled Nanowire Optical Sensor System And Methods Of Use Thereof, which provisional application is incorporated herein by reference in its entirety.

This invention was supported by U.S. Government contract number Phase I SBIR Navy Contract N65540-03-0055 and NSF Phase I DMI-0339668 and portions of this invention are subject to a paid-up license to the U.S. Government.

FIELD OF THE INVENTION

Freestanding metallic nanowires attached to a metallic substrate are disclosed. A method of creating the nanowire structure using an anodized layer is presented. One embodiment of the present invention relates to Surface-Enhanced Raman Scattering (SERS) based sensor heads or devices and systems incorporating such devices, and methods for molecular identification based on SERS.

BACKGROUND OF THE INVENTION

Freestanding metallic nanowires attached to a metallic substrate are disclosed. A method of creating the nanowire structure using an anodized layer is presented. One embodiment of the present invention relates to Surface-Enhanced Raman Scattering (SERS) based sensor heads or devices and systems incorporating such devices, and methods for molecular identification based on SERS. Analytic techniques for detecting, discriminating, and quantifying various molecular species in blood, air, water, and soil samples or analytes are generally known. These include fluorescence microscopy, chromatography, photometry and spectroscopy. Spectroscopy is a commonly used analytical technique for screening chemical and biological samples in laboratories and hospitals. It involves the measurement of the interaction of radiant energy with matter and the interpretation of the interaction. Interpretation of the spectra produced by various spectroscopic instruments has been used to provide fundamental information on atomic and molecular energy levels, the distribution of species within those levels, the nature of processes involving change from one level to another, molecular geometries, chemical bonding, and interaction of molecules in solution. Comparisons of spectra have provided a basis for determining qualitative chemical composition and chemical structure, and for quantitative chemical analysis.

Raman spectroscopy (relying upon Raman effect) provides definitive information about the molecular structure of a material by investigating its vibrational spectrum. Different molecular species exhibit different Raman spectra. In fact, isomers of the same molecular species can be distinguished by this technique.

Surface Enhanced Raman Scattering (SERS) techniques may employ small structured materials. Noble metal nanoparticles exhibit very strong optical absorption in the ultraviolet through the visible range of the spectrum, which is not observed in their bulk counterparts. The absorption leads to tremendous electric field enhancement at the particle surface and in the regions between neighboring nanostructures. This field enhancement affect is utilized in SERS, by employing nanostructured materials to boost the Raman signal intensity. SERS techniques have often led to increases in the effective Raman cross-section by factors of $10^{14}$-$10^{15}$, allowing the Raman spectra of single molecules to be probed in relatively short times (e.g., tens of seconds).

SUMMARY OF THE INVENTION

The present invention discloses a surface enhanced Raman scattering analysis system and methods for detection of target molecules in a test sample using the analysis system and a sensor for the same. The system has a SERS sensor containing an optical substrate and an array of often functionalized high aspect ratio nanowires disposed on the optical substrate. The nanowires are preferably cylindrical and/or solid structures, and are often formed from a metal, such as, silver, nickel, iron, gold, cadmium, copper, or the like, or a semiconductor, such as silicon, Germanium, GaAs or the like. Typically, the nanowires have a length ranging from about 5 nm to about 5 microns. An illumination source (e.g., diode laser excitation source or optical fiber laser excitation source) and optical data collection portion may also be included as part of an analysis system. The nanowires are often chemically functionalized so as to detect molecular species or biological agents in a test sample.

A method for detection of molecular species or biological agents in a test sample is also provided that uses the analysis system of the present invention having a SERS sensor formed in accordance with one aspect of the invention. The method includes contacting the nanowires on the sensor with a sample to be analyzed, illuminating an optical substrate, and collecting optical data from the system following the illumination.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein:

FIG. 3 is an enlarged perspective view, similar to FIG. 1, showing the interaction of a biomolecule with a portion of the nanowires;

DETAILED DESCRIPTION OF THE INVENTION

Figure 1:
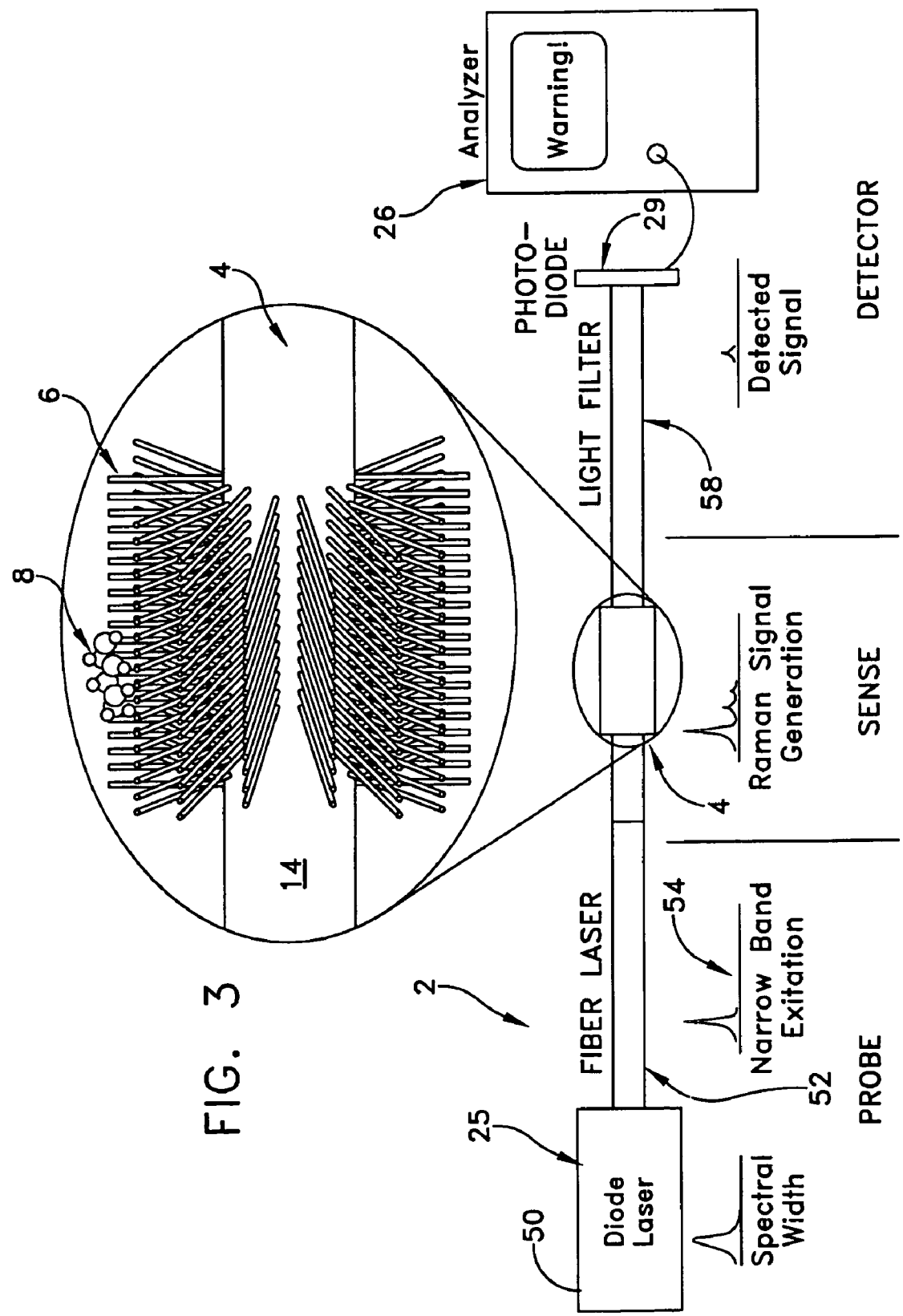
FIG. 1 is a schematic representation of a SERS analysis system, including a nanowire sensor integrated directly on to an optical fiber to maximize the optical coupling efficiency and decrease the detector size, and where the nanowires have been chemically functionalized to bind targeted biomolecules.
Figure 2:
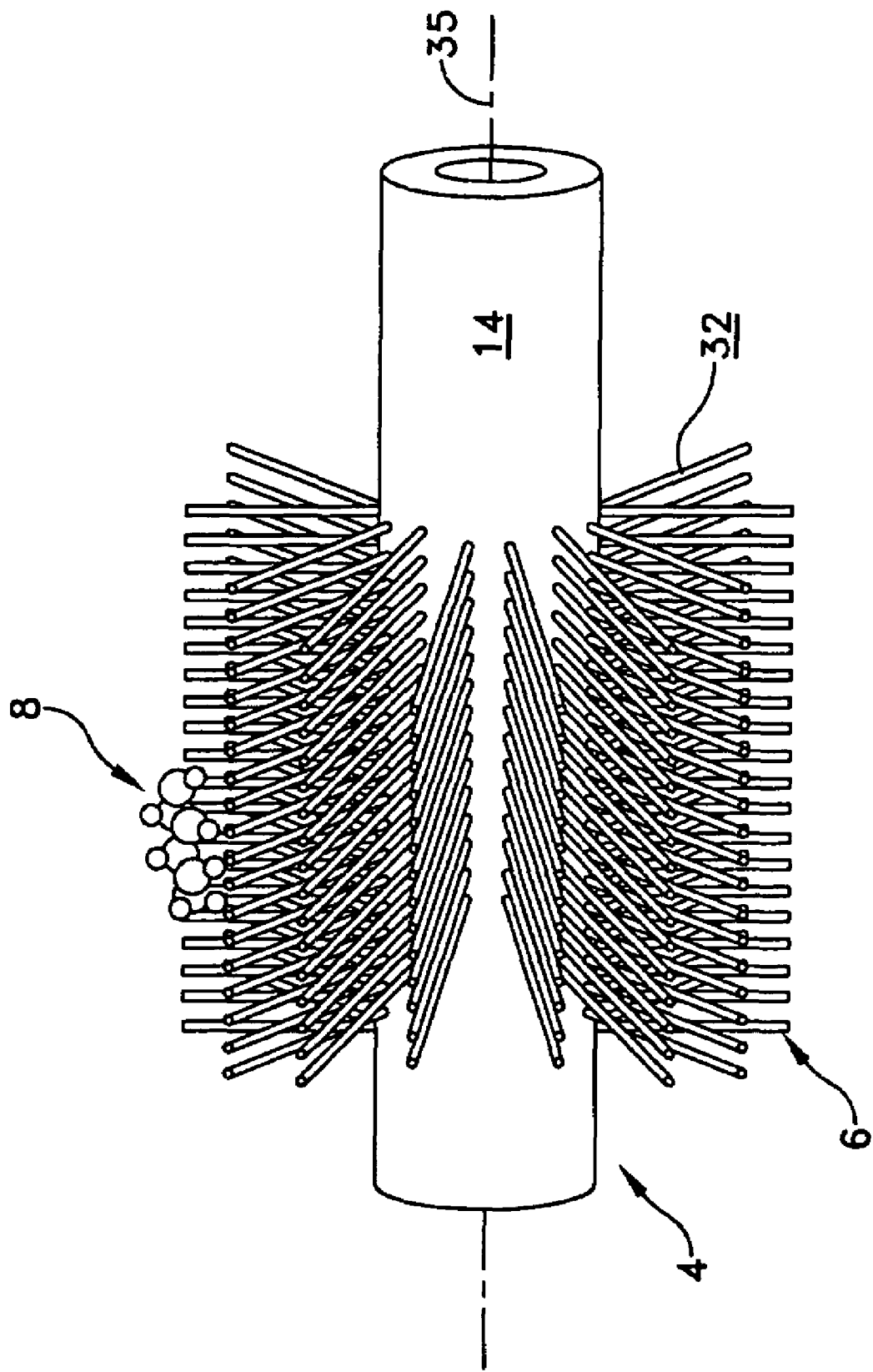
FIG. 2 is a perspective side view of a Surface Enhanced Raman Scattering (SERS) sensor formed according to one embodiment of the invention.

Referring to FIGS. 1 and 2, a SERS optical sensor system 2 is provided that includes an optical sensor 4 comprising an array of nanowires 6 for detecting, discriminating, and quantifying molecular species 8 using spectroscopy methods. SERS optical sensor system 2 often uses an illumination or excitation source 25, SERS optical sensor 4 and an optical data collection and analysis portion 26. A diode laser or optic fiber laser may often be used as excitation source 25. SERS optical sensor 4 may be integrated into a system including an optical detector 29. The preferred detector for a SERS optical sensor system 2 is photodiode array 29 fabricated from InGaAs technology. These InGaAs diode arrays will operate in the near infrared allowing the use of high power diode lasers. The advantage of near infrared Raman is that luminescence that interferes with the Raman spectrum can be avoided since the near IR photon energy is too low to generate these excitations. A portable version of SERS optical sensor system 2 with handheld data collection and/or analysis units can be used for testing various samples.

Throughout this disclosure the term "nanowires" refers to high aspect ratio, solid wire structures (made from, for example, a metal or a semiconductor) having a length in the range from about 5 nm to about 5 μm with appropriate, application specific diameters. It is preferred that nanowires 6 are made of a metal, such as for example, silver, nickel, iron, gold, cadmium or copper. Preferred, semiconductors for use as nanowires 6 are silicon, Germanium and GaAs. Nanowires 6 in an array can all be of the same length, or vary in length. Nanowires 6 in a SERS optical sensor 4 often comprise dimensions that coincide with a fundamental resonance of the exciting optical wave or a harmonic (integer multiple) of the fundamental resonance mode and/or can create a resonant cavity for the exciting optical wave or for surface plasmons in the nanowire. SERS optical sensor 4 often includes nanowires 6 with a geometry adapted for plasmon field enhancement and large reduction of plasmon damping. A typical SERS optical sensor 4 formed in accordance with one embodiment of the present invention comprises an array of nanowires 6 formed about a surface 14 of an optical fiber 16 serving as a substrate (FIG. 2). Arrays of nanowires 6 are often produced using a templating technique (FIGS. 5 and 6) that is dependable and relatively easy to incorporate into a manufacturing environment.

The versatility in processing allows nanowire arrays to be formed with uniform wire density using a variety of substrates 20, including flat solid substrates or, the outer surface 14 of an optical fiber 16. Substrates 20 may include any of the optical materials well known in the art for use in optical systems, such as glass, sapphire, etc., or other conductive substrates. In addition, one can control the length and diameter of nanowires 6 in an array, which facilitates tuning the array and optical sensor 4 to a particular excitation wavelength. Additionally, the density of nanowires 6 may be chosen to provide an array with a number of nanowires per unit area adapted to maximize an output signal. For example, the lengths may range from 5 nm to 200 microns, preferably up to 100 μm long, and wire densities can be up to $10^{11}$ cm$^{-2}$ or even up to $10^{12}$ cm$^{-2}$.

Nanowires 6 manufactured according to the methods of the present invention are preferably chemically functionalized to recognize or to trap selective chemical species 8 in a test sample. Functionalization involves depositing one or more suitable active chemicals on the surfaces 32 nanowires 6. The chemicals may include, but are not limited to thiocyanate, thiol alkanea, peptides, proteins, antibodies (monoclonal and polyclonal), DNA, RNA, PNA, histidine, streptavidin, biotin and inorganic elements, ions or compounds and other suitable chemicals capable of reacting or binding with counterparts in the test sample. In one embodiment, nanowires 6 are coated on their respective outer surface 32 by submersing the array in a solution of the functionalizing material. One or more monolayers may be added to surface 32 of each nanowire 6 in this way. Additional layers may include antibodies and antigens. In one embodiment of the invention, SERS optical sensor 4 has an array of nanowires 6 oriented normal, i.e., at or about 90°, with respect to the longitudinal axis 35 of an optical fiber (FIGS. 1 and 2). The array of nanowires 6 can be used as a test platform for single or multiple chemical or biological species 8, for drug testing, or for environmental testing.

Figure 5:
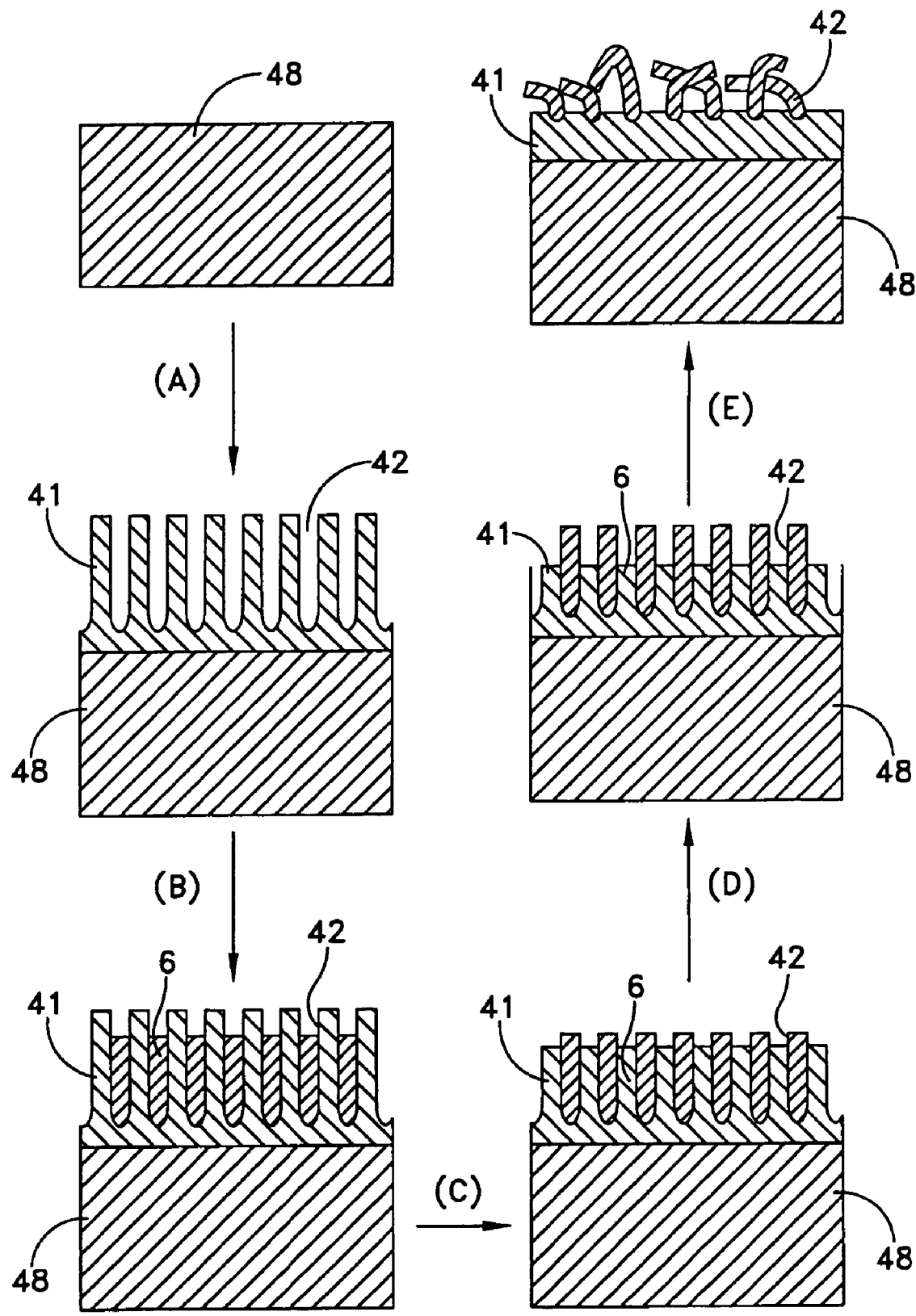
FIG. 5 is a schematic representation to show how nanowire SERS substrates are formed including (a) AAO template being formed, (b) pores being filled with metal, (c) AAO being partially etched to expose the well-ordered nanowire tips, (d) more of the nanowires being exposed, and (e) the entire nanowire exposed.
Figure 6:
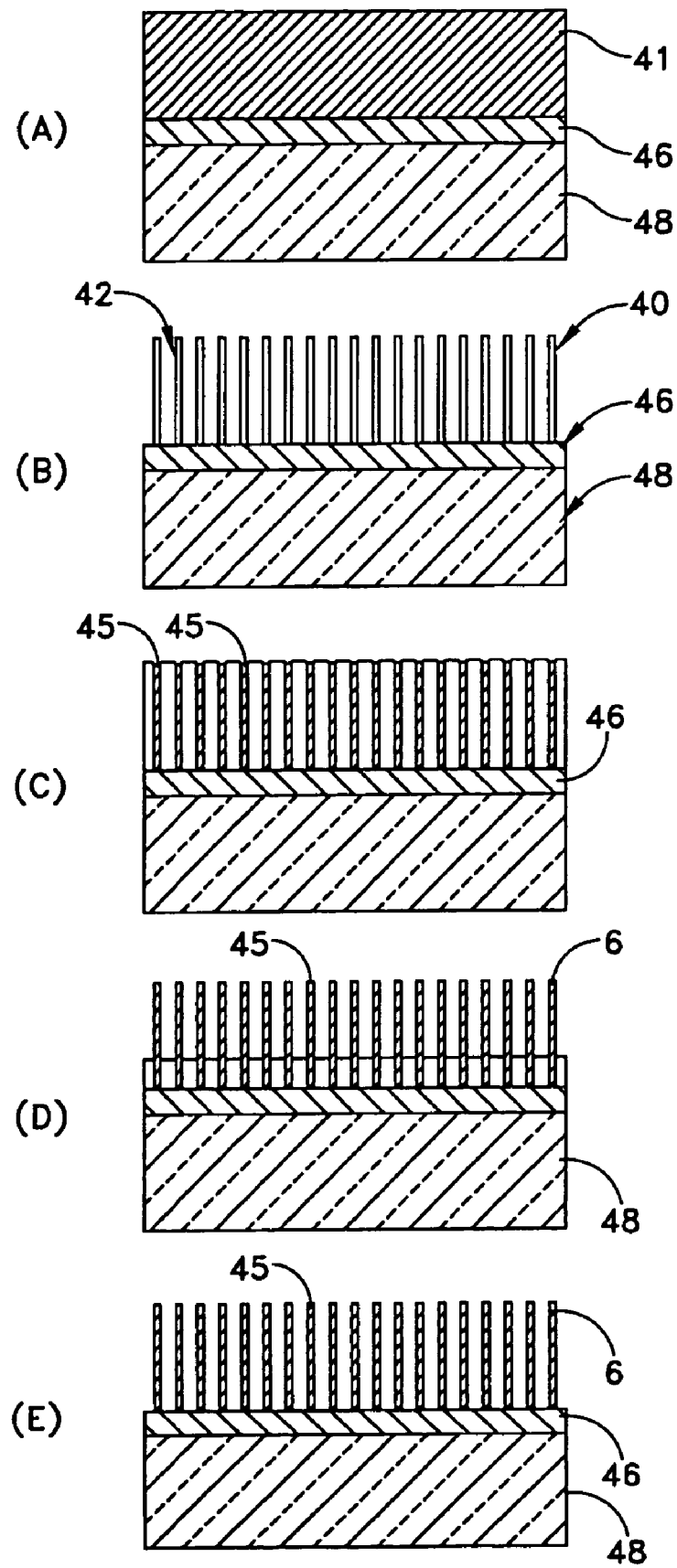
FIG. 6 is a schematic representation of yet another method for forming nanowires in accordance with the present invention.

In another specific aspect, the present invention provides an SERS optical sensor 4 with nanowires 6 grown on a suitable substrate 20 within a removable template such as a removable self-assembled template. For example, an alumina template 40 can be used in which a series of blind holes or nanobores 42 have been formed, e.g., by etching (FIGS. 5 and 6). Nanowires 6 are grown within nanobores 42 in alumina template 40 formed according to a method of the invention using electrochemical processes so that nanowires 6 are individually attached to substrate 20 after complete removal of alumina template 40 (FIGS. 5 and 6). A conductive layer 46 and a glass substrate base 48 may be disposed below template 40 (FIG. 6).

The self-organizational properties of certain materials (e.g., anodic aluminum oxide (AAO)) are useful for nanowire production in the present invention. When aluminum 41 is anodically oxidized in an acidic electrolyte, a uniform and oriented porous-structured layer, i.e., nanobores 42, is formed with nearly parallel pores organized in a hexagonal geometry. Thus, in an aspect of the present invention, nanowires 6 may be formed on optical fiber 16 in part by coating a surface 14 with a desired thickness of aluminum 41 (for example, 1-3 □m) and then anodizing the aluminum metal forming a porous Al$_2$O$_3$ sheath around optical fiber 16. Aluminum 41 may be sputter coated onto surface 32 of optical fibers 16. Prior to aluminum coating, a thin (e.g., about 10-100 nm) strike layer 46 of a desired metal, such as gold, is deposited onto surface 32 of optical fiber 16 for later use as the electrode for electrochemically forming nanowires 6, i.e., for the electrodeposition of gold to form gold nanowires. Optically transparent conductors may also be used as strike layer 46 electrode, e.g., indium-tin-oxide (ITO). Other such optically transparent materials that are useful in the present invention are ZnO:M and V$_2$O$_5$.

The AAO can be produced with the desired nanobore diameter, spacing and depth to control the dimensions of nanowires 6 formed on AAO template 40. The depth of nanobores 42 is controlled by the duration of the anodization process. The separation of nanobores 42 is controlled by the anodization voltage and nanobore diameter is controlled by the duration of a post anodization chemical etch process, as will be disclosed in further detail hereinbelow. The array of nanobores 42 is formed by self-assembly. For example, arrays of gold (Au) nanowires 6 may be produced using porous AAO with nanobore diameters of about 20-80 nm, nanobore depths of about 1-5 µm, and a center-to-center spacing of about 20-250 nm. Spectral analysis performed on the nanowire arrays can be used to determine the proper dimensions that will optimize these parameters for plasmon resonance.

Figure 4:
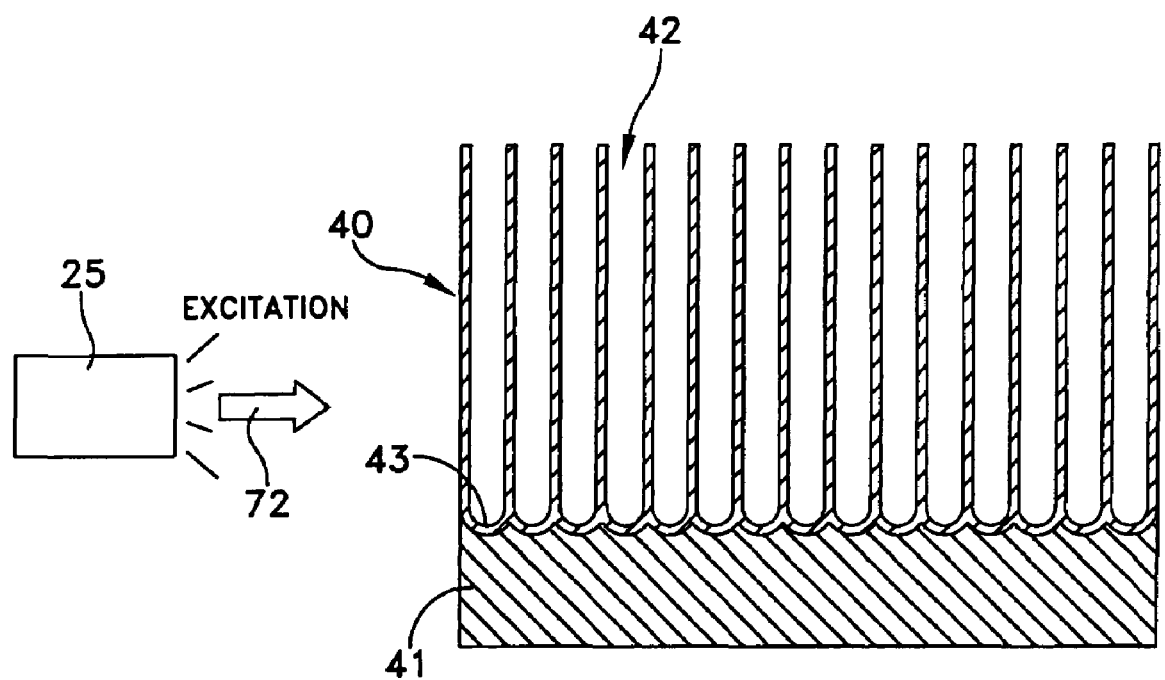
FIG. 4 is a schematic cross-sectional view of a self-assembled porous anodic aluminum oxide (AAO) material produced on aluminum metal, that serves as a template for the deposition of metals to form the nanowire arrays of the present invention.

A SEM micrograph of a porous anodic aluminum oxide template 40 will reveal the relationship between nanobore diameter and anodization voltage. FIG. 4 shows a cross-section of AAO template 40 as produced on aluminum metal 41. As aluminum 41 is anodized, Al$_2$O$_3$ physically forms in a uniform porous formation to create template 40. The structure can be used directly to template nanowires 6, a barrier layer 43 can be removed to form nanowires 6 in contact with aluminum metal 41, or the oxidation can be carried out until all the metal is consumed and nanobores 42 completely penetrate the structure.

In a representative anodization process, the aluminum layer is anodized in a solution of 0.3-wt % oxalic acid at 2° C. The anodization is carried out until all the aluminum metal 41 is consumed and nanobores 42 in alumina template 40 penetrate through to strike layer 46 (FIGS. 5 and 6). The typical anodization rate is about 1 µm/hour. Anodization is performed at about 20-1000 V DC depending upon the desired nanobore diameter and spacing. A brief post anodization etch in phosphoric acid will remove any residual Al$_2$O$_3$ from the bottom of nanobore 42, exposing strike layer 46. For example, following anodization, the AAO nanobores 42 can be widened and strike layer 46 cleared in a 0.5 wt % solution of phosphoric acid. It is possible to accurately control the diameter and center-to-center spacing of nanobores 42 by adjusting the anodization voltage, and the electrolyte composition and concentration. For example, by optimizing voltage, electrolyte composition and concentration, and nanobore widening, the diameter and pitch may be controlled over a range of about 10-250 nm. Nanobore depth is often a linear function of the anodization time and can be extended up to several hundred microns.

Gold nanowire arrays may also be formed using the basic AAO templating technique shown schematically in FIGS. 5 and 6, except the anodization is carried out until nanobores 42 completely penetrate aluminum metal 41. Briefly, in FIG. 5, step (a) is to create porous AAO template structure 40. Step (b) fills nanobores 42 in template 40 with metal by e.g., electrodeposition techniques. The anodized layer is partially removed by chemical etching in step (c) using phosphoric acid, leaving an ordered array of nanowire tips protruding from an Al$_2$O$_3$ matrix of nanobores 42 and producing a SERS active surface. The Al$_2$O$_3$ can be further removed in step (d) while still maintaining ordered, well-aligned nanowires 6. Further removal of the Al$_2$O$_3$ in step (e) exposes ever-increasing lengths of nanowires 6. If the Al$_2$O$_3$ structural support is completely removed, nanowires 6 may collapse. The length and diameter of nanowires 6 may be such that it most effectively leads to Raman enhancement. Preferably, arrays of gold nanowires 6 are produced about the circumference of optical fiber 16. Gold nanowires 6 may be from about 20 nm to about 80 nm in diameter, with a center-to-center spacing of about 20-250 nm, and an exposed length of about 1-5 □m.

In an embodiment of the invention, gold nanowires 6 may be prepared inside porous AAO templates 40 by standard AC electrolysis conducted at, for example, about 100-1000 Hz at a level of about 0.1-30 V$_{ac}$ using a function generator. Gold nanowires 6 may also be prepared inside template 40 using a DC electrodeposition technique, for example, using 1.2 Vdc applied to the substrate as the cathode in the electrodeposition bath. A typical electrodeposition bath may have a solution of potassium gold cyanide and citric acid that is pH controlled using potassium hydroxide and phosphoric acid. Alternatively, a gold sulfide plating solution can be used. After plating, the Al$_2$O$_3$ matrix can be partially etched back in phosphoric acid to expose a desired length of each nanowire 6 leading to a structure similar to that shown in FIG. 2. In a preferred embodiment, nanowires 6 will have direct optical contact with optical fiber 16. Optical fibers 16 that are coated with nanowire arrays may be imaged using SEM at various stages of production process to determine their dimensions and structural integrity and to document the work. By way of further example, Ag, Ni, Fe, Au, and Cu nanowire arrays may be patterned on a variety of substrate materials using the AAO templating technique. Nanowire arrays using porous Al$_2$O$_3$ as template 40 have been successfully engineered using electrodeposition of cadmium, iron, gold, silver, copper, nickel, and other metals from aqueous solution. Nanowire arrays can also be built using electronics fabrication methods such as photolithography and electrodeposition.

EXAMPLES

The following examples further illustrate the present invention, but of course should not be construed as in any way limiting its scope. The examples below are carried out using standard techniques, that are well known and routine to those of skill in the art, except where otherwise described in detail. The examples are illustrative, but do not limit the invention.

Example 1

Engineering of SERS Active Gold Nanowires on Glass Substrates

An AAO template and gold nanowires of 90 nm diameters, 2 µm long were produced as follows:

The base material used is a multilayer structure comprising a standard 75 mm by 25 mm glass microscope slide, a layer of indium tin oxide (10 to 20 Ohms per square), and a layer of aluminum 1 to 1.5 μm thick. The gold nanowire arrays were produced on these substrates using the following procedure:

1. Prepare anodization bath using 0.1 to 0.3 weight percent oxalic acid solution. The concentration of the solution used to anodize the aluminum layer is dependent on voltage being used to anodize. Higher voltages require lower concentrations. Cool the bath to 5° C. by placing in an ice bath.

2. Clean aluminum substrate with acetone and alcohol followed by a DI water rinse for 1 minute.

3. Blow dry with air.

4. Mask off interface line on the sample with acrylic paint to protect areas not to be anodized.

5. Set up the data acquisition system to acquire data during processing.

6. Set power supplies to the required voltage.

7. Place the sample in the anodization bath so that the masked area falls slightly below the liquid-air interface of the bath.

8. Connect electrical connections. Positive lead attached to aluminum layer to be anodized, negative lead to a stainless steel mesh counter electrode.

9. As the initial oxide layer forms on the surface of the aluminum the measured current level drops rapidly to a "resting" level where anodization takes place.

10. As the anodization front reaches the back of the aluminum layer the current level will decrease slightly, and then start to increase. The increase in the current is associated with the thinning of the barrier layer at the bottom of the channels as it is consumed by the anodization process.

11. When the current level reaches twice the "resting" current, the power is removed from the cell to stop the anodization process. The sample appears uniformly translucent at the end of the process.

12. The sample is removed from the anodization bath and rinsed with DI water for 1 minute.

13. The sample is placed in a beaker filled with DI water to keep the anodized channels filled with water. This is important to achieve uniform widening of the channels as well as uniform filling during the plating process.

After the porous matrix has been formed in the aluminum layer the channels are widened using a pore widening etch. The etch serves two purposes: first, to widen the channels to the desired diameter and second, to remove the remainder of the barrier at the bottom of the channels to provide direct electrical contact to the ITO layer for electrodeposition. A specific process used to widen the pores created from the above anodization procedure is:

1. Prepare a 5 vol % phosphoric solution for pore widening.
2. Heat the solution to 37° C.
3. Place sample in the phosphoric solution so that the edge of the masked area lies below the liquid-air interface.
4. Allow the sample to remain in the bath for 7-10 minutes using mild agitation.
5. Remove sample and rinse in DI water for 1 minute.
5. Return sample to DI water bath to keep pores wet before plating step.

Electrodeposition of metals into the channels is accomplished using a standard electroplating bath. All metals, semiconductors and insulators that can be deposited using an electrodeposition process may be deposited into the channels. The specific materials of interest for Surface Enhanced Raman Scattering devices are the transition metals most notably copper, silver and gold. Below we enumerate a specific process used to deposit gold into the porous matrix.

1. Pre-Heat TSG-250 gold sulfite plating solution to 55-60° C.
2. Turn on the power supply and set up plating parameters:
   a. Frequency 20 kHz
   b. Amplitude 400 mV
   c. Offset 800 mV
3. Place the sample in the plating bath so that a portion of the masked area lies beneath the liquid interface.
4. Connect electrical leads. Positive to a gold anode and negative to the ITO layer on the sample.
5. Plate the sample for 2 minutes 30 seconds with mild agitation.
6. Remove sample from plating bath.
7. Rinse residual plating solution from the sample for 1 minute followed by air blow dry.

Once the channels have been filled with metal, the remaining alumina matrix is removed using the following process:

1. Heat a 5 vol % phosphoric solution to 37° C.
2. Place the plated sample in the solution so that the masked area is inserted just beneath the solution-air interface.
3. Etch the sample for 45 to 60 minutes.
4. Remove the sample from the phosphoric solution and rinse in DI water for 1 minute.
5. Allow to air dry to prevent damage to the wire array.

Example 2

Functionalization of the Nanowires to Preferentially Bind Hemoglobin Present in Blood Samples The nanowire arrays may be functionalized in any number of solutions to form molecular bridges to other target molecules. Here we detail a process for functionalizing the surface of gold nanowires with potassium thiocyanate (KSCN) as a bridging molecule for hemoglobin. In solution KSCN dissociates to become $K^+$ and $SCN^-$.

1. An array of gold nanowires was immersed in a 1 molar aqueous solution of potassium thiocyanate.
2. The nanowire array is allowed to sit in solution for 30 minutes to allow the KSCN molecules to fill all the locations on the surface of the gold nanowires. The sulfur atom in the $SCN^-$ radical preferentially binds to the gold nanowire.
3. The nanowire array is removed from the KSCN solution and rinsed in DI water for 5 minutes.

Infrared data of the nanowire array after this treatment show that the SCN radicals are still present on the surface after rinsing, strongly suggesting the presence of the SCN attached to the gold nanowire.

In part, functional groups disposed on nanowires 6 depend on the sample to be screened or the type of assays. Screening can involve detection of biochemical substances 8, such as proteins, metabolites, nucleic acids or biological agents such as fungi, bacteria and viruses. For example, nanowires 6 can be functionalized for applications in genomics, proteomics and SNP assays, medical diagnostics, drug discovery screening, and detection of biological and chemical warfare agents.

Specifically, a nanowire 6 may be functionalized by attaching a bridging molecule and/or a reactive molecule to nanowire using solution chemistry. The nanowire array is submersed in a solution containing a concentration of the bridge molecules large enough to coat surfaces 32 of nanowires 6 with a monolayer of the bridge molecule. In the specific case of gold nanowires 6, the bridging molecule has a thiol (sulfur containing) group that preferentially binds to the gold surface. The opposite end of the bridging molecule contains a chemical group that preferentially attaches to additional bridge molecules or the sensor target.

A specific embodiment uses mercaptoundecanoic acid which contains both a thiol group and a carboxylic acid group. The thiol group binds to gold nanowire 6 and the carboxylic acid group can bind to antibodies or antigens specific to the molecule the sensor is targeting. Other molecules can also be used. For example, potassium thiocyanate can be used as a bridge for hemoglobin detection. The functionalization process is simply finding the molecules that will create the chemical bridge and bind to both nanowire 6 and the target/additional bridge molecules. A specific advantage of nanowire 6 geometry is that the bridging molecules will populate entire surface 32 of nanowire 6 providing many more sites for target binding to occur. Binding along the entire length of nanowire 6 enables a greater volume of target molecules to be sampled, increasing detection efficiency.

The first step in functionalizing nanowire arrays may be the formation of a self-assembled monolayer (SAM). As an exemplary embodiment of the invention, gold nanowire arrays may be chemically functionalized to bind with hemoglobin. To functionalize the gold nanowire arrays to preferentially bind hemoglobin, a SAM is deposited onto surface 32 of each gold nanowire 6 by reacting a sulfur group, for example, in thiocyanate or thiol alkane with the gold. The sulfur group of the thiocyanate ion ($SCN^-$) will bind to surface 32 of each gold nanowire 6. The iron in the hemo-group of the hemoglobin will bind to the cyanate portion of the ion. For example, a 0.1 M aqueous solution of thiocyanate with a pH of 7 may be used at room temperature.

If needed, a different SAM using a thiol alkane (carbon chain with a sulfur group attached to the end) with a cyano-functional group on the terminal end ($HS-CH_2-CH_2-CH_2-\ldots CH_2-CH_2-CN$) may also be deposited in place of, or in addition to using thiocyanate. The cyano group will be facing away from surface 32 of nanowires 6. so that the length of the alkane chain can be controlled to accurately penetrate the protein. Different lengths of the alkane chain functional groups may be prepared to determine the optimum length that will reach into the hemo crevice to bind to the iron. For example, gold nanowire arrays may be submerged in an ethanol solution of 1 mM thiol alkane (or aqueous solution of thiocyanate) for several minutes at room temperature. Nanowires 6 are then removed from solution, rinsed with ethanol and dried under a stream of nitrogen. This should achieve 90 to 95% coverage of nanowires 6 with the SAM and the attached functional groups.

Characterization of the resulting thiol alkane (or thiocyanate) layer can be done using, for example, infrared reflection-absorption spectroscopy and cyclic voltammetry. The infrared spectrum should show absorption peaks due to the thiol alkane (or thiocyanate) that are not present on untreated gold nanowires 6. Cyclic voltammetry in a buffer solution employing modified gold nanowires 6 as the working electrode often display oxidation and reduction peaks due to the presence of thiol alkane (or thiocyanate) on gold nanowires 6. These measurements are performed on nanowire arrays with and without the functional groups attached. After preparation of the SAM covered, functionalized gold nanowires 6, which will serve as the platform for the attachment of hemoglobin, they may be stored under purified nitrogen.

After the functionalization has been performed, the ability of the cyanate group to bind to hemoglobin may be determined. For example, this can be accomplished by exposing (e.g., by immersing) a functionalized nanowire array to an aqueous solution of a commercial sample of hemoglobin dissolved in a phosphate buffer of pH 7.4 and then measuring the infrared spectrum at several positions on the surface of the array. Variations in the intensity of the infrared absorption from one position to another is an indication of how uniformly the hemoglobin has bound to the surface of nanowires 6. The presence of hemoglobin attached to the nanowires 6 can be further verified using cyclic voltammetry to estimate the percent coverage of the hemoglobin on surfaces 32. Imaging of the array with the attached hemoglobin may be also be done using SEM.

Figure 7:
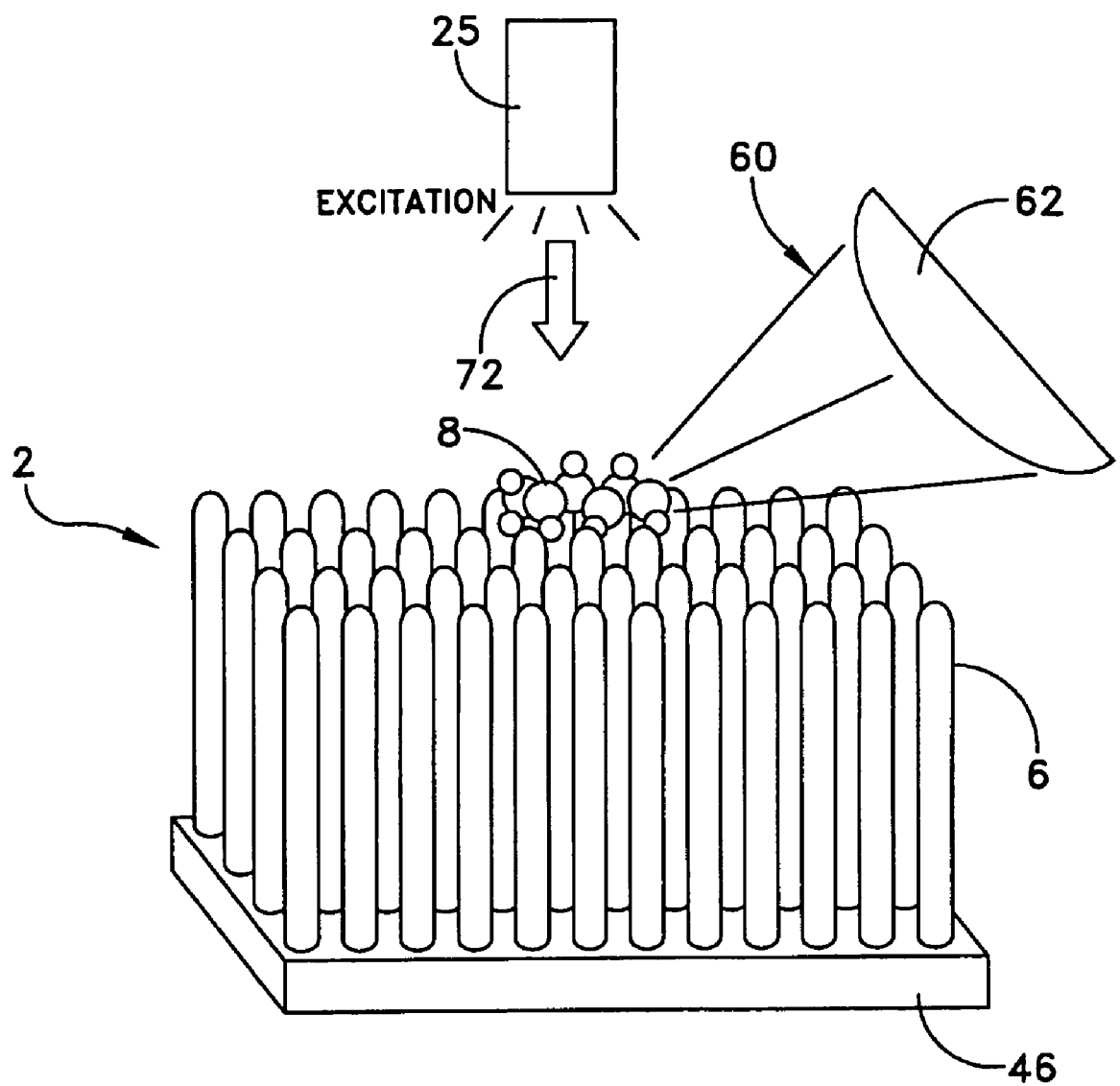
FIG. 7 is side perspective view of one embodiment of SERS sensor formed in accordance with the present invention and illustrating optical paths for excitation and data collection.

In one embodiment, as shown schematically in FIG. 7, SERS optical sensor 2 has an array of nanowires 6 on a flat solid substrate 46. Incident light 72 from excitation source 25 interacts with, and excites nanowire 6 which in turn causes molecule 8 (located on surface 32 due to that surface's prior functionalization) to vibrate and thereby give off Raman shifted emissions 60 that are collected by optical elements 62 for further processing.

A large array of nanowires 6 may be used to probe a sample of solution deposited onto the array. The nanowire array can act as a fluid wick spreading the solution throughout the array for maximum exposure of the solution to surfaces 32. Different areas of the array may be functionalized with different surface treatments to attach one or more specific molecules. In this way, the nanowire array may be used to analyze the concentration of one or more species in a solution. Such an optical sensor 2 is often useful for drug testing where only small quantities of drugs are available for test.

Figure 8:
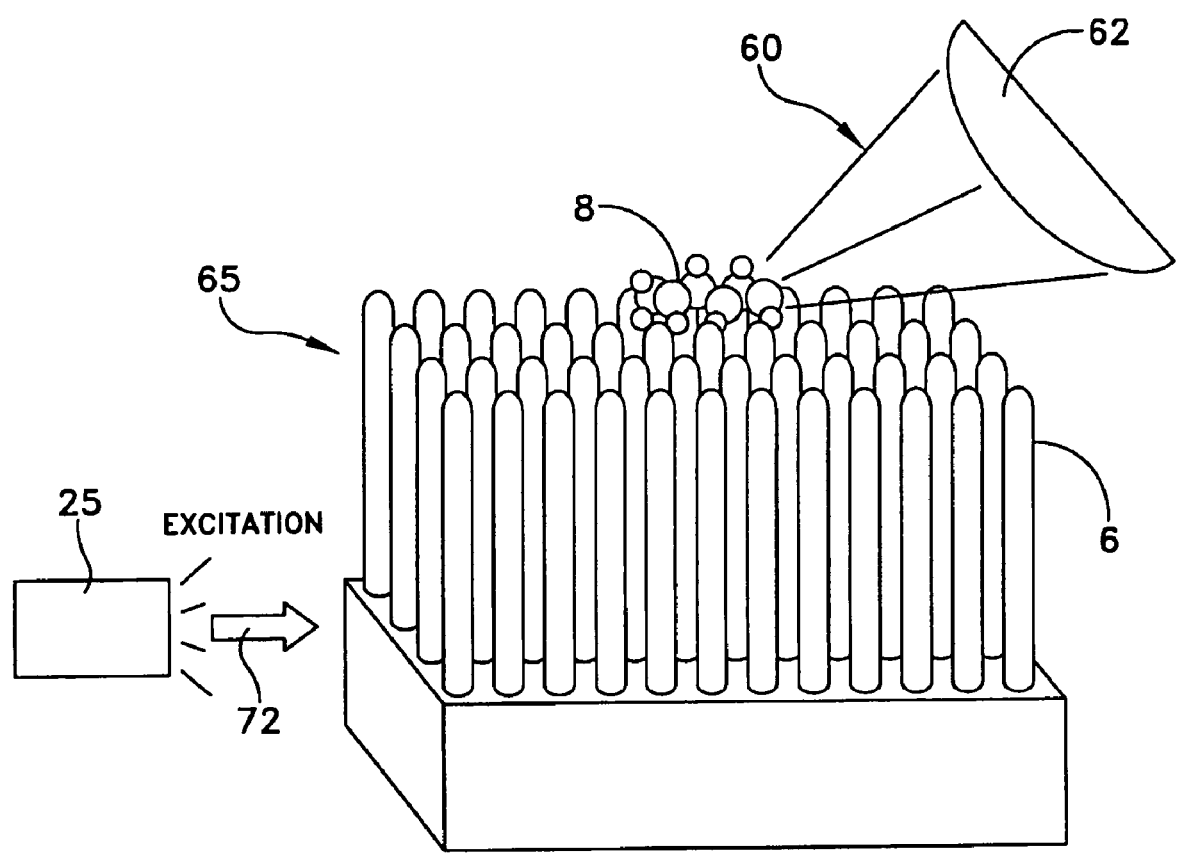
FIG. 8 is a side perspective view, similar to that of FIG. 7, of yet another embodiment of SERS sensor and optical paths for excitation and data collection.
Figure 9:
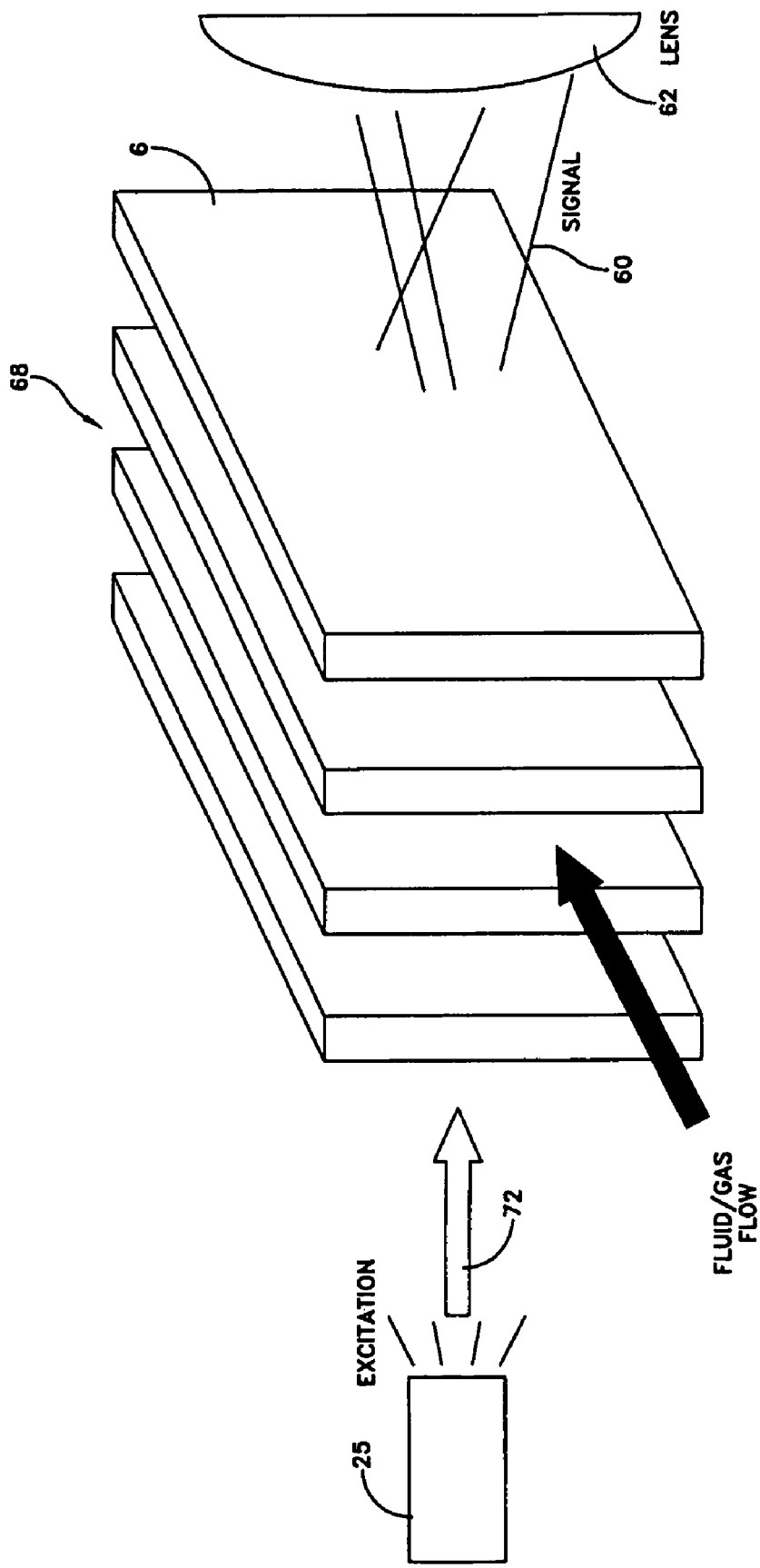
FIG. 9 is a side perspective view of a number of SERS sensors of the type shown in FIG. 8, assembled into a parallel array with this plurality of SERS sensors comprising a fluid/gas flow analysis system.

In another embodiment, as shown schematically in FIG. 8, an SERS optical sensor 65 has an array of nanowires 6 on a flat transparent substrate 48, e.g., glass. Excitation light 72 is directed through substrate 48 to excite nanowires 6, with emissions from molecules 8 on the nanowire side of substrate 68 being collected by optical elements 62 for further processing. Such a sensor may be well suited for air and water monitoring systems for buildings or large public areas. Numerous plates 68 of nanowires 6 may be assembled into a parallel array (See FIG. 9) with a single excitation source being used from outside array of plates 68. Since the plates are transparent to excitation source 25, the single excitation source can be used to probe many plates within an air or water stream without encumbering the stream. In the case of air sampling, a fluid, such as water, may be used to permeate the nanowire array to improve collection of airborne chemicals and/or biological agents.

Figure 10:
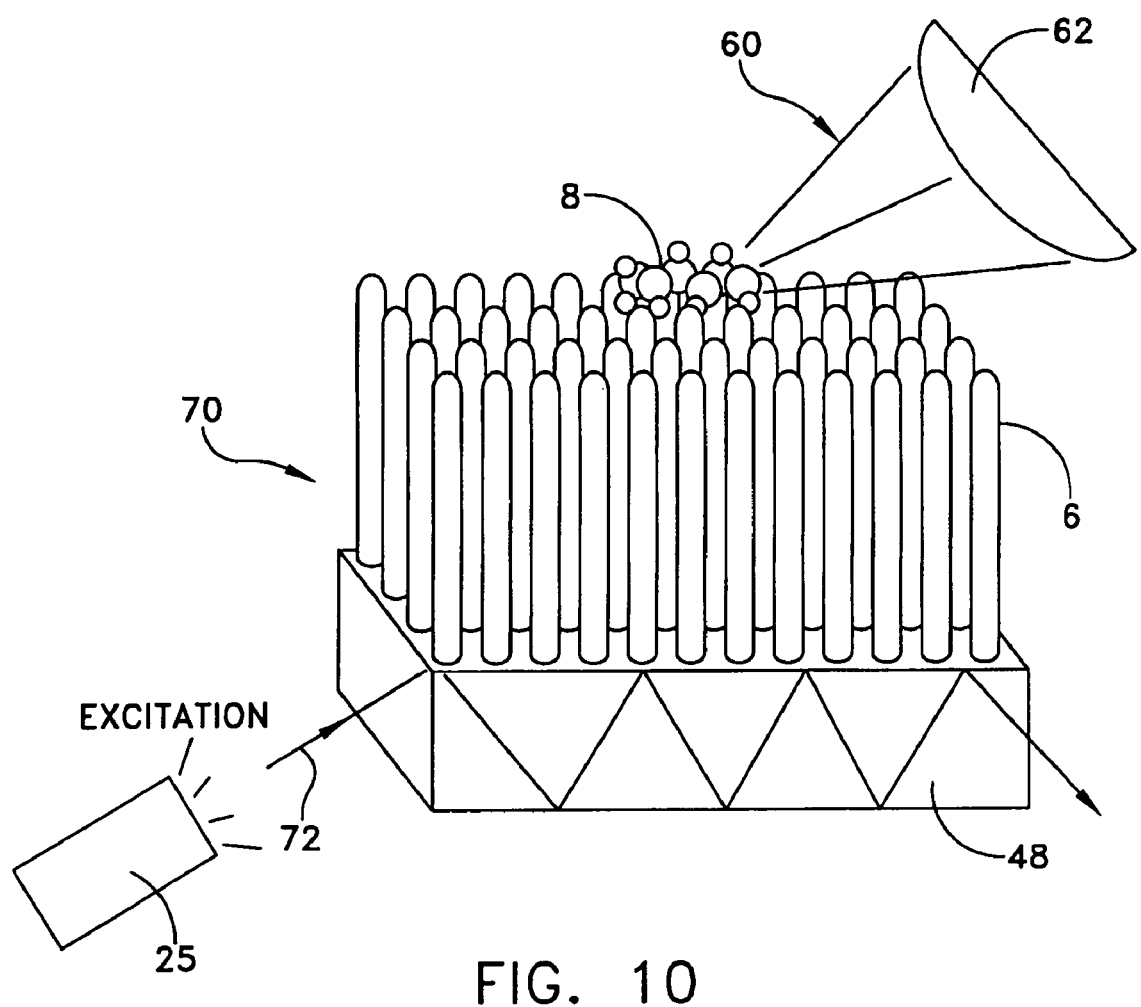
FIG. 10 is a side perspective view, similar to that of FIG. 7, of another embodiment of SERS sensor and optical paths for excitation and data collection, where an excitation source is confined to a transparent substrate that is often made of a dielectric material and used as a light guide.

In yet another embodiment, an SERS sensor 70 has an array of nanowires 6 on a flat transparent substrate 48. Excitation light 72 is guided by transparent substrate 48 (FIG. 10) and escapes from the light guide and excites nanowires 6 which in turn causes molecule 8 (located on surface 32 due to that surface's prior functionalization) to vibrate and thereby give off Raman shifted emissions 60 that are then collected by external optical elements 62. This embodiment may be well suited for a portable system where excitation source power is limited and must be preserved. This arrangement may also be well suited for reducing the effects of sensor fouling.

Figure 11:
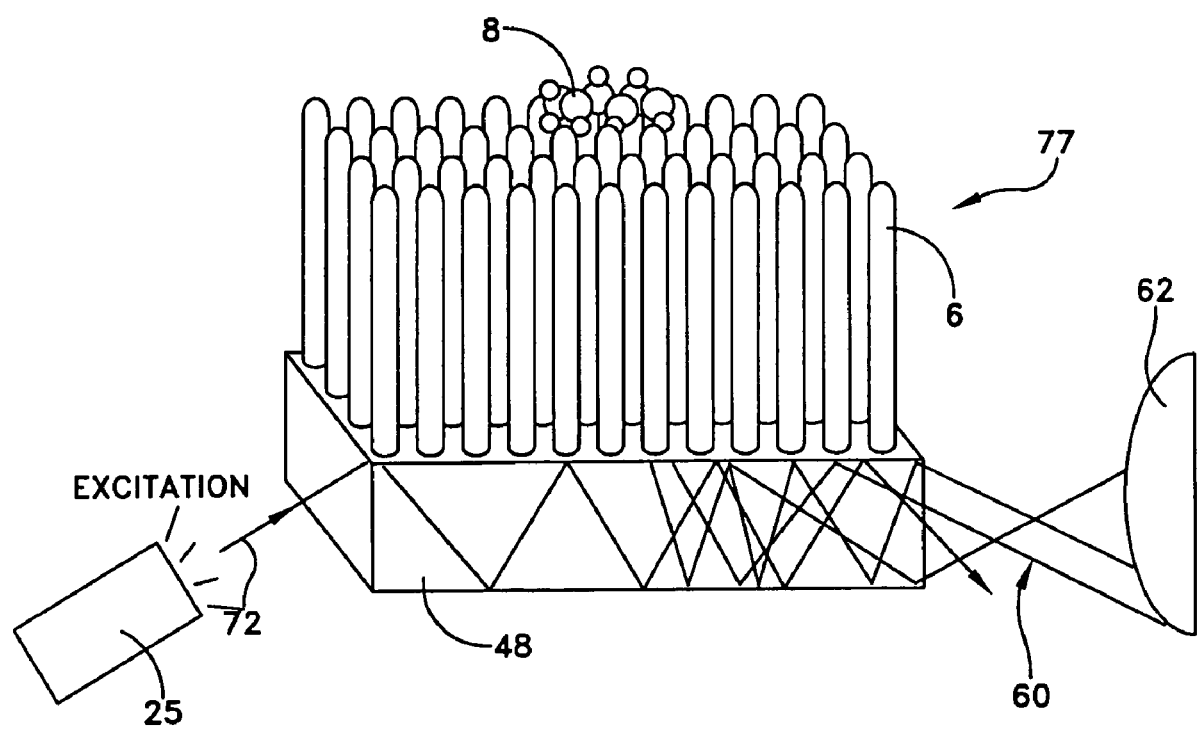
FIG. 11 is a side perspective view, similar to that of FIG. 7, of another embodiment of SERS sensor with a substantially closed optical path.
Figure 12:
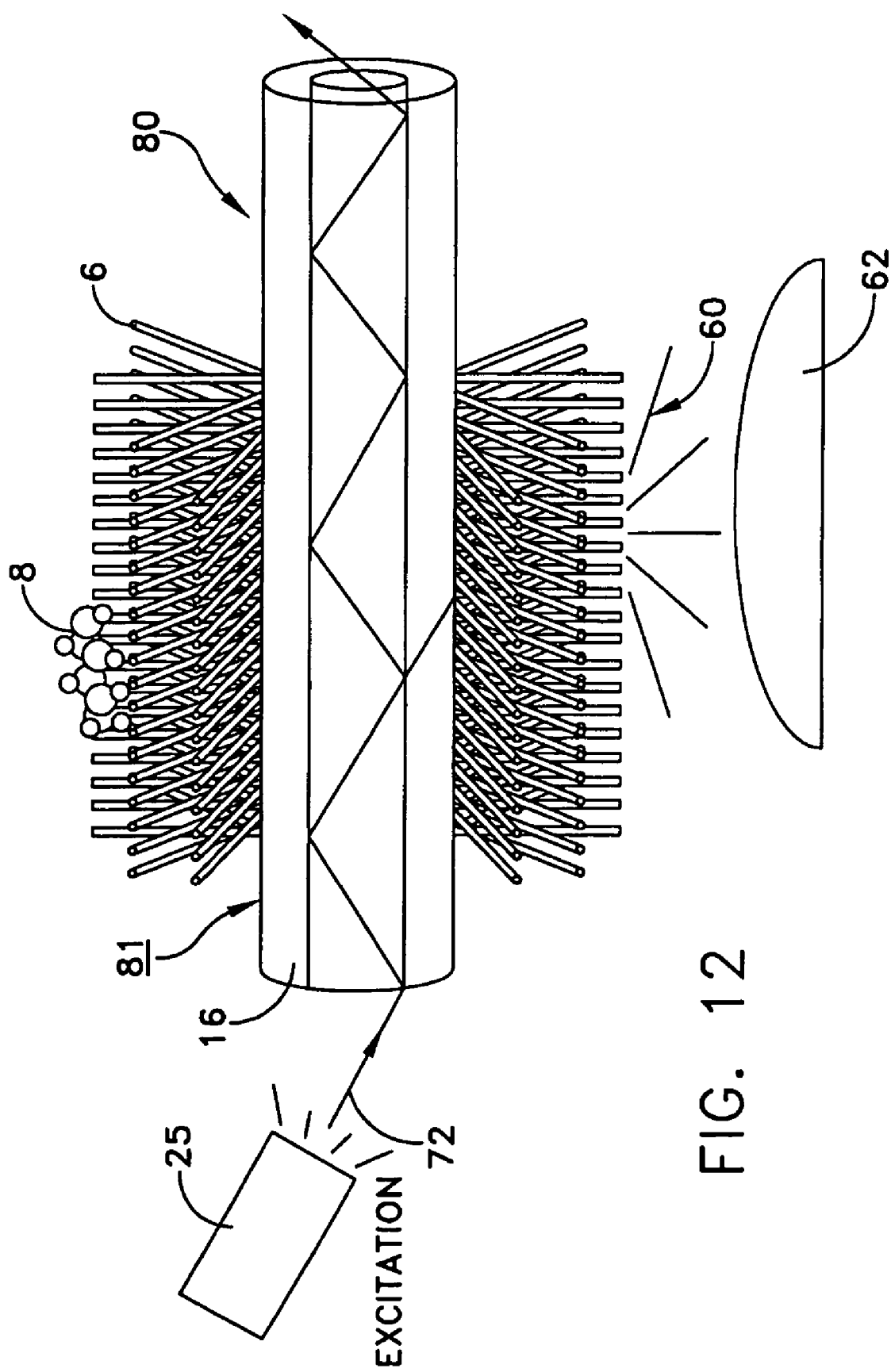
FIG. 12 is a side perspective view, similar to that of FIG. 1, of another embodiment of SERS sensor including an optical fiber as a substrate, when the use of an optical fiber is desirable for maximizing the ratio of the nanowire array area to the excitation source power and for portable applications to preserve battery life.

In a further embodiment, a SERS sensor 77 has an array of nanowires 6 on a flat transparent substrate 48. Excitation light 72 is guided by transparent substrate 48, and escapes from this light guide to excite nanowires 6 which in turn causes molecule 8 (located on surface 32 due to that surface's prior functionalization) to vibrate and thereby give off Raman shifted emissions 60. Raman shifted light emissions 60 from nanowires 6, re-entering the light guide, are then collected (FIG. 11). This arrangement may be well suited for portable systems operating in a dirty environment where fouling may inhibit both the excitation source and the generated Raman signal.

Figure 13:
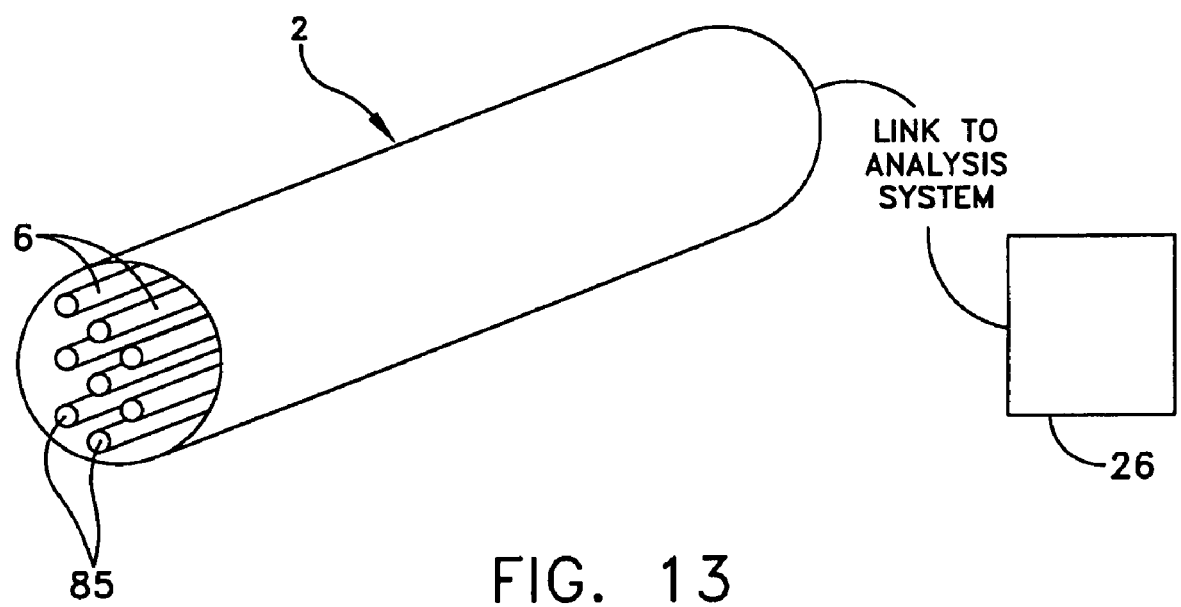
FIG. 13 is a perspective view of a further embodiment of SERS sensor having an array of nanowire SERS optical fiber sensors, where each fiber detects a specific agent and each fiber is excited with its own unique wavelength to maximize the output signal.

In another embodiment, an SERS sensor 80 has an array of nanowires 6 on a shaped transparent substrate 81, preferably an optical fiber 16. Excitation light 72 escaping from this light guide excite nanowire 6 which in turn causes molecule 8 to vibrate and thereby give off Raman shifted emissions 60 which are collected by external optical elements 62. This arrangement forms a low cost disposable sensor that may be bundled to form a chemical/biological sensor suite in portable systems. A sensor may comprise one or more such devices bundled together (as shown in FIG. 13). Custom sensor heads can be constructed to provide custom sensitivity for one or more agents of interest. A reflective enclosure can be used to collect all of the light emitted from the different species, i.e., chemical sensitivities, in fibers 85 in the array.

Figure 14:
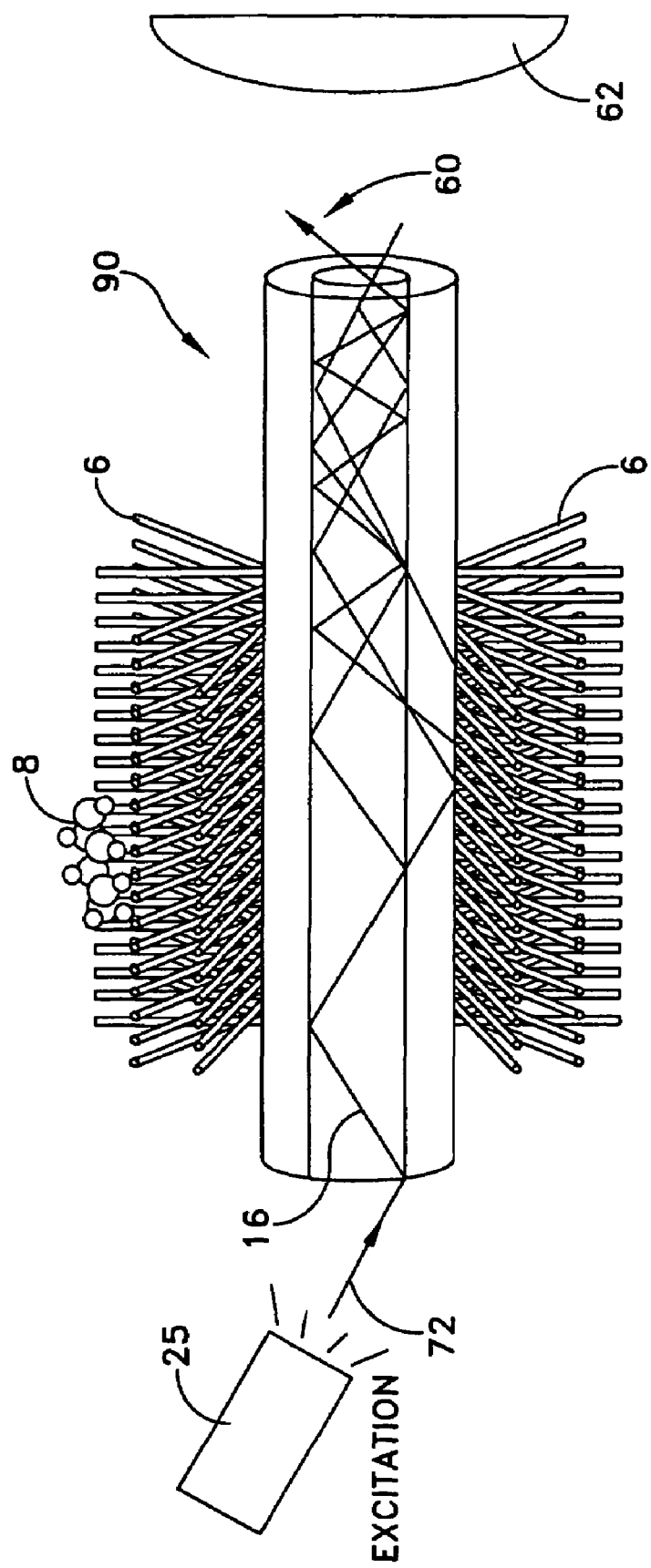
FIG. 14 is perspective view of another embodiment of SERS sensor with a substantially enclosed optical path, optical fiber.

In yet another embodiment, a SERS optical sensor 90 has an array of nanowires 6 on a shaped transparent substrate, preferably an optical fiber. Excitation light 72 is guided by the transparent substrate and excitation light 72 escaping from the light guide excites nanowires 6. Emissions from molecules 8, re-entering the light guide, are collected. This design is least affected by fouling where opaque and nonactive species settle on the nanowire array. This is the preferred embodiment when multiple excitation sources are employed to insure ultra high reliability for detecting a particular species in a diverse background. Multiple fiber sensors are bundled, each with an excitation source of unique wavelength. (FIGS. 13 and 14).

Figure 15:
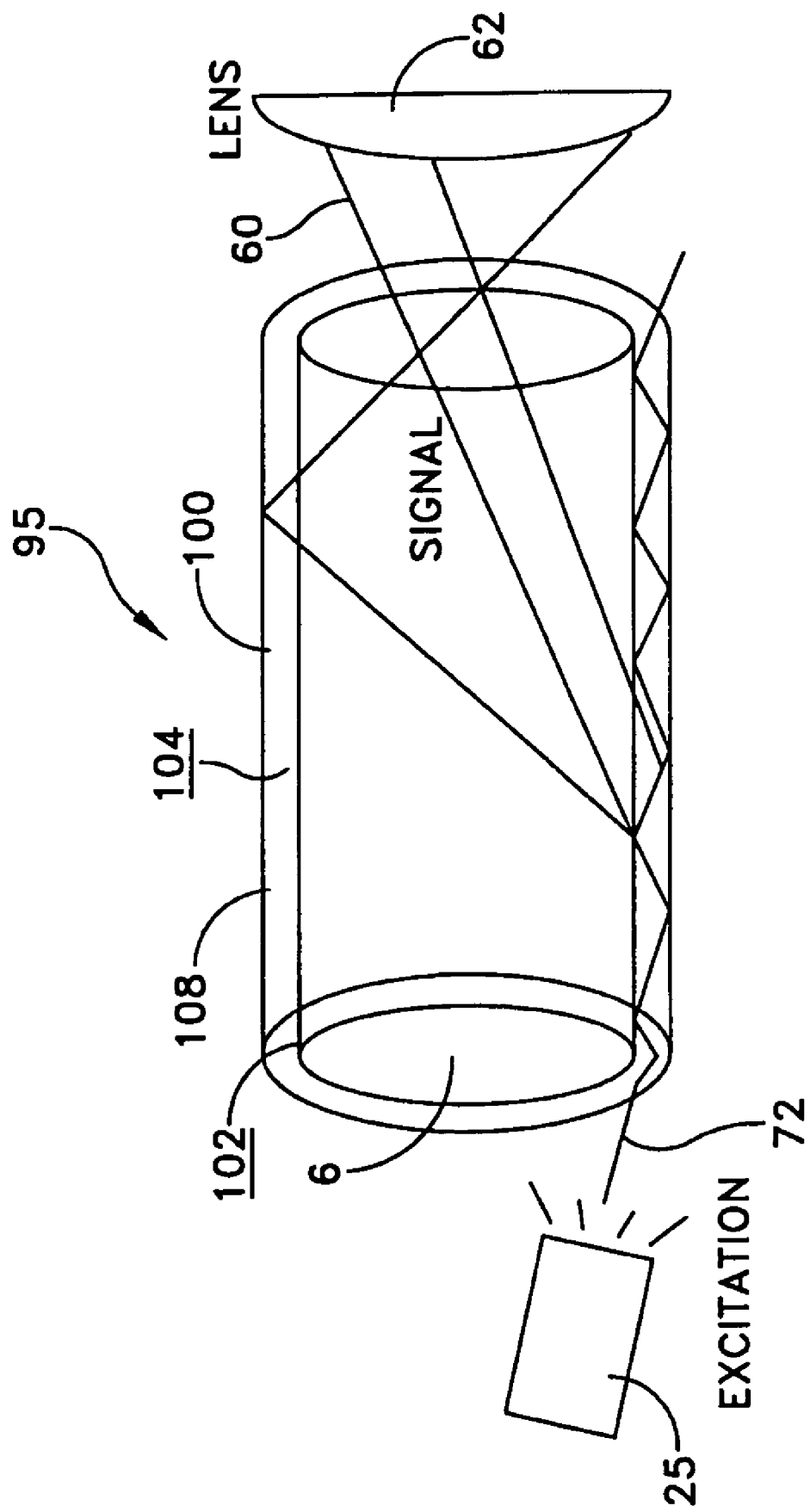
FIG. 15 is perspective view of a hollow tube nanowire SERS detection system, having a large central flow path to enable high volume flow.

In another embodiment, a SERS sensor 95 has an array of nanowires 6 on a shaped transparent substrate, preferably a hollow tube 100. Nanowires 6 are on an inner surface 102 with an outer surface 104 of tube 100 covered by a reflecting layer 108. Excitation light 72 is guided by the walls of tube 100. Excitation light 72 escaping from the light guide 100 excites nanowires 6, and emissions from molecules 8 are collected by external optical elements 62 positioned at one end of tube 100 (FIG. 15).

Figure 16:
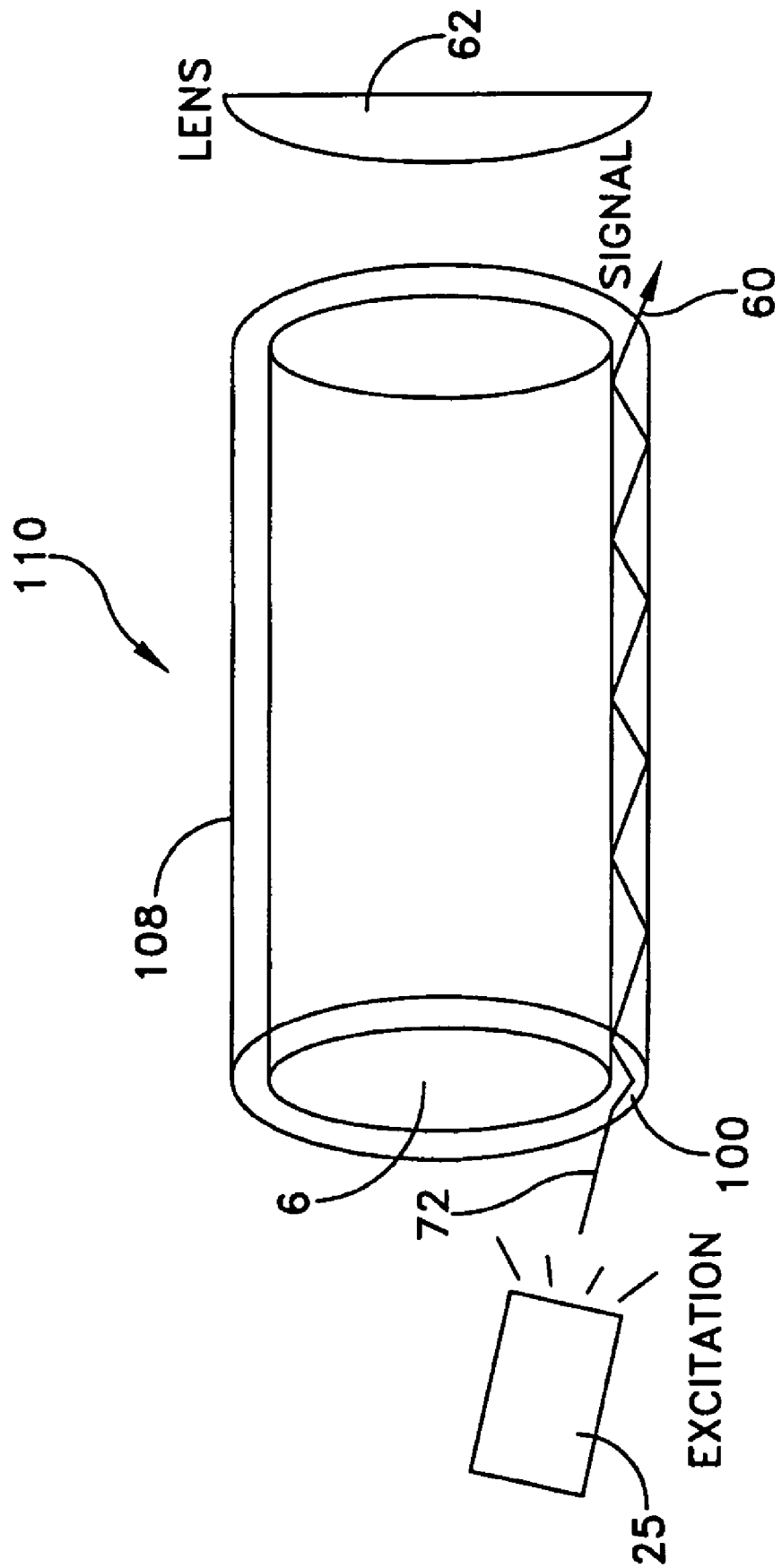
FIG. 16 is perspective view of a closed optical path, hollow tube nanowire SERS sensor adapted to prevent obstruction and to minimize fouling.
Figure 17:
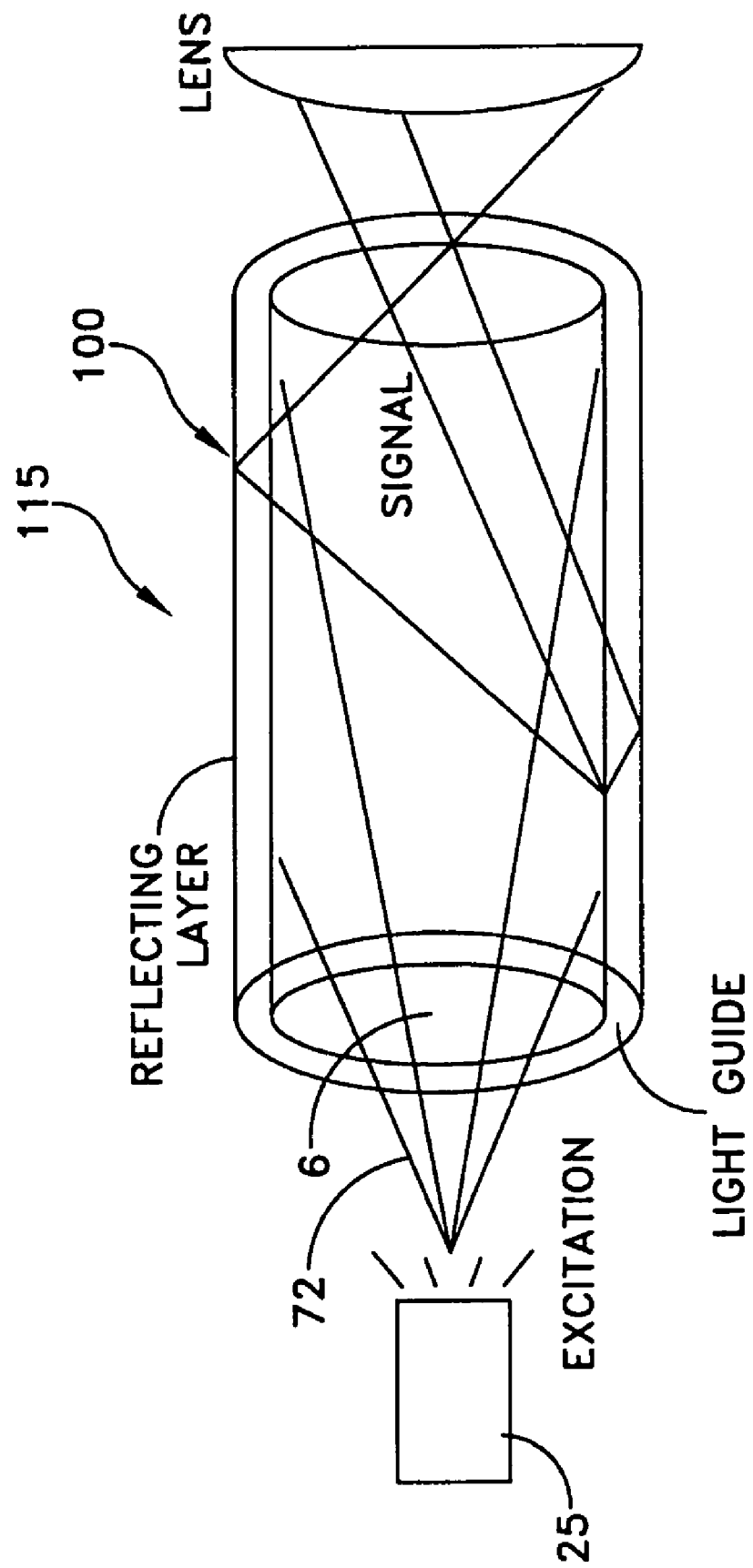
FIG. 17 is perspective view of a hollow tube nanowire SERS sensor with optical paths that are coincident with a fluid/gas flow path.

In a further embodiment, a SERS sensor 110 has an array of nanowires 6 on a shaped transparent substrate, preferably a hollow tube 100. Nanowires 6 are on inner surface 102 with outer surface 104 of tube 100 covered by reflecting layer 108. Excitation light 72 is guided by the walls of tube 100 and excitation light 72 escaping from the light guide excites nanowires 6. Raman shifted light emissions 60 from molecules 8 re-entering the light guide are collected. (FIG. 16).

In another embodiment, an SERS sensor 115 has an array of nanowires 6 on a shaped transparent substrate, preferably a hollow tube 100. Nanowires 6 are on inner surface 104 with outer surface 104 of tube 100 covered by reflecting layer 108. Excitation light 72 may be introduced into the center of tube 100 so as to interact with, and excite nanowire 6 which in turn causes molecule 8 (located on surface 32 due to that surface's prior functionalization) to vibrate and thereby give off Raman shifted emissions 60 that enter the light guide to be collected. This design allows for the maximum excitation power level to be used and has the most efficient light collection. Primary use of this system may be for detecting trace amounts of agents in relatively clean gas/fluids.

Example 3

Raman Measurements to Determine the Sensitivity and Accuracy of Hemoglobin Detection Raman spectra are acquired using the 514.5 nm line of an argon ion laser. The light is directed against the surface of the wire array in the backscattering geometry, but may be directed through the back side of the glass substrate. Data are acquired for two to ten minutes by a single grating monochromater fitted with a linear CCD array with a resolution of 1 $cm^{-1}$. Referring again to FIG. 2, a Surface-Enhanced Raman Scattering (SERS) analysis system 2 formed according to an aspect of the present invention operates as follows. A low-power diode laser 50 that is integrated into a fiber laser cavity 52 creates a narrow bandwidth optical excitation 54 to probe molecular species located adjacent to SERS optical sensor 4. Nanowires 6 act as a type of optical antenna, transferring the light energy from optical fiber 16 to molecules 8 located or trapped on surface 32 of one or more nanowires 6 in the array. This light then excites Raman emission from molecule 8. The Raman spectrum of the molecules provides a unique "fingerprint" for identification, as no two molecular species have the same Raman spectrum. Nanowires 6 formed to the appropriate geometry and dimensions enable the enhanced optical signature of molecular species 8 to be detected using SERS. Raman shifted light that is collected back into optical fiber 16, while probe light is filtered out. For example, excitation source 25 (e.g., diode laser 50) laser is removed from the signal path using a notch filter 58 or other similar optical device placed in the optical signal capture path. The separate, isolated optical path within optical fiber 16 reduces sensor-fouling errors. The emitted Raman spectra are then detected using photodiode spectrometer 29 and the spectrum is analyzed in a manner similar to pattern recognition systems. Analyzer 26 compares the detected spectrum to a database of known spectra, and quantifies the concentration of detected species 8. For example, such a system 2 with nanowires 6 functionalized to bind hemoglobin can be used for detecting, discriminating, and quantifying the molecule in a drop of blood sample used for analysis. A nanowire sensor head formed according to the invention can be integrated with the other optical and electronic components to form a compact and portable hemoglobin monitoring system.

SERS optical sensor system 2 may be based upon arrays of metallic nanowires 6 on a selected substrate (e.g., an optical fiber) and then chemically functionalizing nanowires 6 to bind specific analytes. It will be understood that the present invention may be readily extended to detect and identify other important bio-molecules, nucleic acids, or protein sequences. SERS optical sensor system 2 offers dramatically increased speed and sensitivity for detecting a large range of biologically important molecules, as well as, the potential for in vivo analysis.

Nanowire nanosensors such as optical sensor 4 of the present invention can detect single molecules or chemicals at picomolar concentrations. One of the most practical physical properties of metallic nanowires 6 for use in sensor technology is plasmon resonance. Plasmons are collective electron oscillations that are triggered when electromagnetic radiation is incident upon a metal structure. The resonance is due to a correlation between the wavelength of the incident radiation and the dimensions of the metallic nanowires. The absorption of light often peaks at the plasmon resonance frequency. Without intending to be bound by any particular theory, it is believed that the enhancement is due to the wire geometry acting like a perturbation on a spherical nanoparticle to form a plasmon resonator with modes that lie predominantly along the length of the wire. The nanowire geometry can be assumed to be similar to a prolate ellipsoid for the purposes of surface plasmon modes. In the present invention, nanowires 6 have a size as to match the surface plasmaon modes to the laser frequency being used. Nanowires 6 act as resonant cavities that enhance the strength of the electric field on surface 32 of each nanowire 6. The size of the enhancement is often directly proportional to the quality factor for the mode. A cylindrical geometry of nanowire 6 provides a distinct advantage to nanospheres in that nanowires 6 can be polarized in a specific mode along their length. Nanowires 6 polarized in this way can interact with neighboring nanowires 6 to increase the surface enhancement factor. Often there appear to be a linear relationship between the radius of a metallic cylindrical nanowires 6 and the incident wavelength that governs the resonance effect. As classically derived, the resonant radius is a fraction of the wavelength, and for high-aspect cylinders, the resonance frequency is seemingly independent of the length. In these terms, high aspect ratio nanowires 6 are usually height to diameter of about 5:1 or greater.

While some other factors, such as polarization, may be considered, this example demonstrates a key consideration in engineering nanowires 6 to directly couple light energy from optical fiber 16 to target molecule 8. According to an aspect of the present invention, nanowires 6 may be tuned (formed) to the proper diameter that corresponds to the excitation wavelength resonance used in the Raman analysis. Nanowires 6 are often grown to a specific length, as defined by the depth of in template 40, i.e., the thickness of the anodized layer. The voltage used in the creation of template 40 controls the separation between the nanobores 42 and hence the nanowires 6. The duration of a bore widening etch controls the diameter of nanobores 42 and hence nanowire diameter. The particle size dependence of the optical enhancement from nanoparticles in SERS has been experimentally observed to have a linear relationship with the excitation wavelength.

Nanowire geometry (high-aspect ratio, metallic, cylindrical structure) is desirable for plasmon field enhancement due to the large reduction of plasmon damping found in these structures. Further, SERS is more pronounced in composite groups of nanostructures like arrays of nanowires 6. Importantly, organized particle arrays, unlike random structures, can be tuned to a common plasmon resonance frequency due to coupling between the ordered structures in the array. Plasmon field enhancement is typically large at the ends of nanowires 6 and in the regions between nanowires 6 due to strong electromagnetic coupling where the materials are touching or in close proximity.

Nanowires 6 are often formed in the range from about 5 nm to about 200 nm in diameter and, preferably in the range from about 20 nm to 80 nm in diameter. Nanowires 6 are often spaced between about 5 nm and about 50 μm with a center-to-center spacing of about 20-250 nm. Nanowires 6 formed on substrate 40 may have an exposed length of about 1-5 μm to 10 μm. Nanowire densities may range from about $10^9$ to $10^{12}/cm^2$. With such densities and wire lengths of up to about 10 μm. Nanowire array substrates 40 can have a surface area enhancement factor of 10,000 for SERS, for example.

It is to be understood that the present invention is by no means limited only to the particular constructions herein disclosed and shown in the drawings, but also comprises any modifications or equivalents within the scope of the claims.

What is claimed is:

1. A method for forming a plurality of substantially freestanding nanowires, individually attached at one end to a metallic layer, comprising: (A) forming a plurality of nanobores in an aluminum layer adjacent to the metallic layer by anodizing the aluminum, each said nanobore extending from the interface region of the metallic layer with the anodized aluminum layer to the opposing surface of the anodized aluminum layer; (B) filling at least a portion of said nanobores with a metal substantially the same as the metallic layer and (C) removing substantially all of the anodized aluminum.

2. A method according to claim 1 wherein said filling comprises electrodeposition.

3. The method according to claim 1 where the metal is copper.

4. The method according to claim 1 where the metal is one of Gold, Silver, Nickel, Cadmium or Iron.

5. The method according to claim 1 where metallic layer is a substrate.

6. The method according to claim 2 further comprising determining when an increase in direct anodization current associated with the thinning of the barrier layer at the bottom of the nanobores has occurred; and stopping the anodization in response to such determination.

7. The method according to claim 1 further comprising etching the nanobores prior to the growing step to remove any barrier between the bore and the substrate.

8. The method according to claim 7 where the removal is accomplished using the etchtant phosphoric acid.

9. The method according to claim 1 where in the growing step, the nanowires are grown to protrude past the opposing surface.

10. The method of claim 1 where the metal is copper and the anodized aluminum is removed from the nanowire array.

11. The method of claim 10 where the substrate is a conductor.

12. The method of claim 11 where the conductor is copper.

13. The method according to claim 6 where the determination step is comprised of detecting when the anodization current has reached approximately twice the resting current.

14. The method according to any of claims 1 or 4 further comprising: functionalizing the plurality of nanowires by depositing a bridging or reactive molecule to said nanowires.

15. The method according to claim 14 where the bridging or reactive molecule is an SAM.

16. The method according to claim 15 where the bridging or reactive molecule is KSCN.

17. The method according to claim 16 where the SAM uses a thiol alkane.

18. The method of claim 1 where the nanowires are grown to between more than one micron and about 10 microns in length.

19. The method of claim 1 where the nanowires are grown to between 1 micron and 200 microns in length.

20. The method of claim 1 where the nanowires have a diameter between approximately 20 and approximately 300 nanometers.

21. The method of claim 1 where instead of anodizing an aluminum layer to form the nanobores, a metal distinct from the metal used for the nanowire is anodized.

22. The method of claim 5 where instead of using an anodizing an aluminum layer to form the nanobores, a metal distinct from the metal used for the nanowire is anodized.

* * * * *

UNITED STATES PATENT AND TRADEMARK OFFICE
CERTIFICATE OF CORRECTION

| | | |
|---|---|---|
| PATENT NO. | : 7,713,849 B2 | Page 1 of 1 |
| APPLICATION NO. | : 11/206632 | |
| DATED | : May 11, 2010 | |
| INVENTOR(S) | : Youssef M. Habib and John Steinbeck | |

It is certified that error appears in the above-identified patent and that said Letters Patent is hereby corrected as shown below:

In the drawings, Sheet 1, Fig. 1, the phrase underneath reference numeral 54 that reads "Narrow Band Exitation" should read and be changed to --Narrow Band Excitation--.

Column 7, Line 10: Please delete the "." at the end of the phrase "Cool the bath to 5°C.".

Column 9, Line 34: Please delete the "." at the end of the phrase "facing away from surface 32 of nanowires 6.".

Column 14, Line 56: The portion of Claim 22 reading "anodizing an aluminum layer" should read and be changed to --anodized aluminum layer--.

Signed and Sealed this

Thirteenth Day of July, 2010

David J. Kappos
*Director of the United States Patent and Trademark Office*